United States Patent
Fu et al.

(10) Patent No.: US 8,372,613 B2
(45) Date of Patent: Feb. 12, 2013

(54) METHODS AND COMPOSITIONS FOR ETHANOL PRODUCING CYANOBACTERIA

(75) Inventors: Pengcheng Patrick Fu, Honolulu, HI (US); Jason Dexter, Baltimore, MD (US)

(73) Assignee: Algenol Biofuels Inc., Bonita Springs, FL (US)

( * ) Notice: Subject to any disclaimer, the term of this patent is extended or adjusted under 35 U.S.C. 154(b) by 1051 days.

(21) Appl. No.: 12/160,770

(22) PCT Filed: Jan. 16, 2007

(86) PCT No.: PCT/US2007/001071
§ 371 (c)(1),
(2), (4) Date: Dec. 2, 2008

(87) PCT Pub. No.: WO2007/084477
PCT Pub. Date: Jul. 26, 2007

(65) Prior Publication Data
US 2009/0155871 A1    Jun. 18, 2009

Related U.S. Application Data

(60) Provisional application No. 60/758,683, filed on Jan. 13, 2006.

(51) Int. Cl.
*C12P 7/06* (2006.01)
*C12N 1/21* (2006.01)
(52) U.S. Cl. ..................................... 435/161; 435/252.3
(58) Field of Classification Search .................. None
See application file for complete search history.

(56) References Cited

U.S. PATENT DOCUMENTS

| | | | |
|---|---|---|---|
| 5,000,000 | A | 3/1991 | Ingram |
| 5,028,539 | A | 7/1991 | Ingram |
| 5,270,175 | A | 12/1993 | Moll |
| 6,306,639 | B1 | 10/2001 | Woods |
| 6,699,696 | B2 | 3/2004 | Woods |

FOREIGN PATENT DOCUMENTS

| | | |
|---|---|---|
| WO | WO 98/39457 | 9/1998 |
| WO | WO 2008/130437 | 10/2008 |

OTHER PUBLICATIONS

D. Lagarde et al. "Increased Production of Zeaxanthin and Other Pigments by Application of Genetic Engineering Techniques to Synechocystic sp. Strain PCC 6803", Applied and Environmental Microbiology 66(1):64-72. (Jan. 2000).*
Qungang Qi, "Application of the *Synechococcus* nir-A Promoter . . . ", Appl. Environ. Microbiology, Oct. 2005, pp. 5678-5684, vol. 71, No. 10.
M. Tichy, "Native isolation of the CcsB protein from *Synechocystis* sp. PCC 6803 . . . ", Photosynthetica, 2003, pp. 583-588, vol. 41, No. 4.
Written Opinion PCT/US2007/001071, Jul. 2008.
Ingram, L.O. and Conway, T., Applied and Environmental Microbiology, vol. 54, No. 2, pp. 397-404 (1998).
Deng, Ming-De and Coleman, J.R., Applied and Environmental Microbiology, vol. 65, No. 2, pp. 523-528 (1999).
Luque et al., Plant Mol. Biol. 21:1201-1205 (1993).
Suzuki et al., Plant Cell Physiol. 34:1311-1320 (1993).

\* cited by examiner

*Primary Examiner* — Rebecca Prouty
(74) *Attorney, Agent, or Firm* — Lawrence B. Ebert; David J. Lorenz; Suzanne G. Jepson

(57) ABSTRACT

The present invention relates to methods and systems for the production of ethanol by cyanobacteria. More specifically, the methods can be used to produce ethanol using genetically engineered light responsive cyanobacteria.

17 Claims, 2 Drawing Sheets

METHODS AND COMPOSITIONS FOR ETHANOL PRODUCING CYANOBACTERIA

REFERENCE TO RELATED APPLICATIONS

The present application is the U.S. National Phase under 35 U.S.C. §371 of International PCT application number PCT/US2007/001071, filed Jan. 16, 2007, which claims the benefit of U.S. Provisional No. 60/758,683, filed Jan. 13, 2006.

CROSS-REFERENCE TO RELATED APPLICATIONS

This application claims the benefit of U.S. Provisional Application Ser. No. 60/758,683, filed Jan. 13, 2006, the entire disclosure of which is incorporated by reference in its entirety.

BACKGROUND OF THE INVENTION

Description of the Related Art

Development of renewable energy is rapidly embraced by society and industry to meet energy growth and emission reduction goals. Since the industrial revolution, the world's economy has relied heavily on fossil fuels as energy sources. Reliance on these energy sources has created several challenging problems, such as reduced supply of fossil fuel resources, environmental pollution and the consequent global warming effect. One alternative to fossil fuels is ethanol. The current world ethanol production is 60% from sugar crops, 33% from other crops and 7% from chemical synthesis. Traditional biomass ethanol production processes require vast quantities of arable land and energy input requirement for the growth of the feedstock. Furthermore, traditional fermentation methods release considerable quantities of $CO_2$ as a byproduct of the fermentation process. For example, a 40 MMGY (million gallons per year) biomass ethanol plant may release 121,000 tons of $CO_2$ each year into the environment (BBI, 2003). This greenhouse gas will worsen the global warming effect.

Bioethanol has recently surged to the forefront of renewable fuels technology. It provides a viable alternative to petroleum based fuels, offering control over both production and consumption processes. In addition, ethanol derived from biological systems is particularly attractive because it can be readily integrated into numerous existing infrastructures; considering both production and fuel industries. Various methods for ethanol production by living organisms have been investigated. The production of ethanol by microorganisms has, in large part, been investigated using the yeast *Saccharomyces cerevisiae* and the obligately ethanogenic bacteria *Zymomonas mobilis*. Both of these microorganisms contain the genetic information to produce the enzymes pruvate decarboxylase (pdc) and alcohol dehydrogenase (adh), which are used to produce ethanol from pyruvate, a product of the glycolytic pathway. Woods et al. (U.S. Pat. Nos. 6,306,639 and 6,699,696; see also Deng and Coleman, "Ethanol Synthesis by Genetic Engineering in Cyanobacteria" *Applied and Environmental Microbiology* (1999) 65(2):523-428) disclose a genetically modified cyanobacterium useful for the production of ethanol. Woods et al. report an ethanol production level of 5 mM after 30 days of culture.

It is therefore desirable to find a simple, efficient and cost-effective biological system for producing substantial amounts of ethanol.

SUMMARY OF THE INVENTION

The technologies mentioned above suffer from various flaws. For example, the systems disclosed by Woods et al. suffer from low ethanol production levels, long fermentation times, and instability.

In some embodiments, what is needed is a simple, efficient and cost-effective system for producing substantial amounts of ethanol. The present invention relates to methods, compositions, host cells, and vectors for the optimization of ethanol production and tolerance of a host cell to economically relevant ethanol concentrations.

A nucleic acid construct is disclosed in accordance with some embodiments of the present invention. The nucleic acid sequence comprises: a light responsive promoter, a sequence encoding a pyruvate decarboxylase (pdc) enzyme, and a sequence encoding an alcohol dehydrogenase (adh) enzyme.

An expression vector is disclosed in accordance with some embodiments of the present invention. The expression vector comprises a nucleic acid comprising a light responsive promoter, a sequence encoding a pyruvate decarboxylase (pdc) enzyme, and a sequence encoding an alcohol dehydrogenase (adh) enzyme.

A host cell is disclosed in accordance with some embodiments of the present invention. The host cell comprises an expression vector comprising a nucleic acid comprising a light responsive promoter, a sequence encoding a pyruvate decarboxylase (pdc) enzyme, and a sequence encoding an alcohol dehydrogenase (adh) enzyme.

A genetically engineered cyanobacterium is disclosed in accordance with some embodiments of the present invention. The cyanobacterium comprises a construct comprising nucleic acid sequences encoding pyruvate decarboxylase (pdc) and alcohol dehydrogenase (adh) enzymes, wherein the cyanobacterium is capable of producing ethanol in recoverable quantities greater than about 10 mM ethanol after a 5 day fermentation.

A method of producing ethanol is disclosed in accordance with some embodiments of the present invention. The method comprises: culturing in a culture medium cyanobacteria, the cyanobacteria containing a construct comprising DNA fragments encoding pdc and adh enzymes obtained from the *Zymomonas mobilis* pLOI295 plasmid; and accumulating ethanol in the culture medium in an amount greater than about 10 mM ethanol after a 5 day fermentation.

Figure 1:
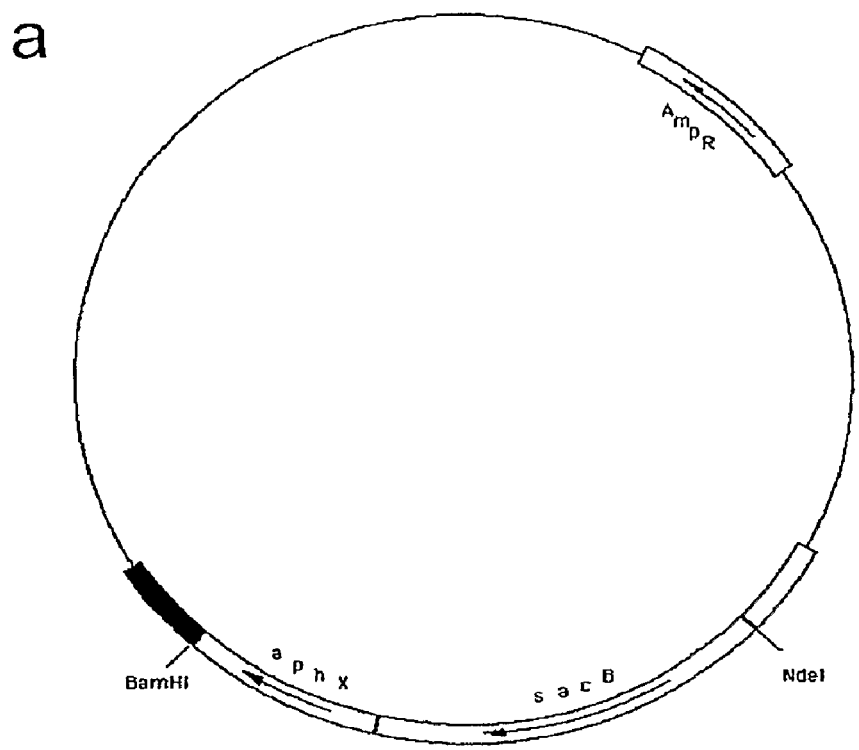
FIG. 1 shows the map of the plasmid constructs (a) pPS-BAIIKS and (b) pLOI295, used to create pMota.
Figure 1:
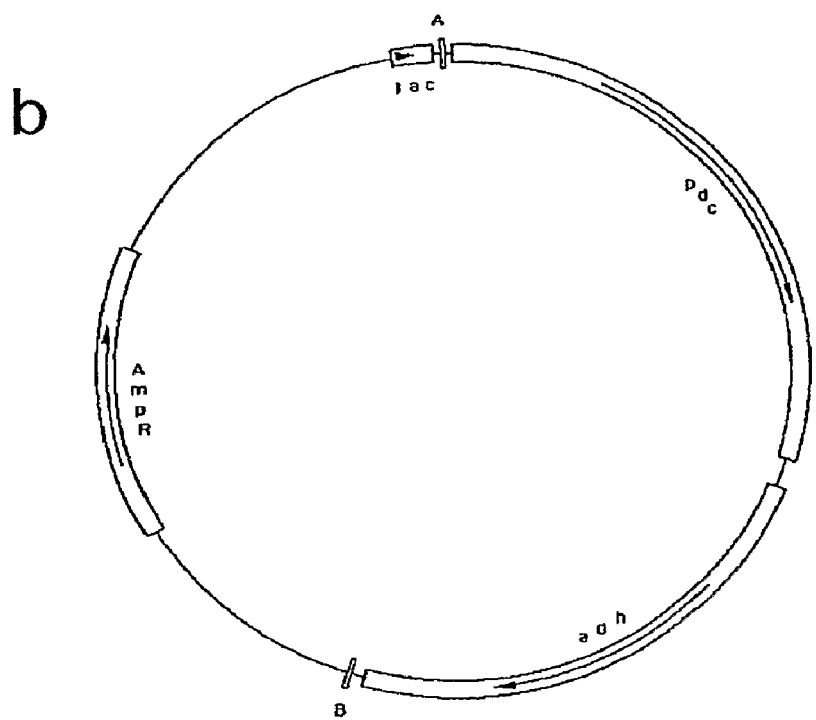

While the subject matter of this application will now be described in detail with reference to the figures, it is done so in connection with the illustrative embodiments. It is intended that changes and modifications can be made to the described embodiments without departing from the true scope and spirit of the subject invention as defined in part by the appended claims.

DETAILED DESCRIPTION OF THE PREFERRED EMBODIMENT

I. Introduction

Nucleic acid sequences, vectors, host cells, and methods for the production of high levels of ethanol by cyanobacteria are disclosed in accordance with preferred embodiments of the present invention.

Ethanol production from cyanobacteria using sunlight, $CO_2$, and inorganic nutrients (possibly diverted from a wastewater stream) is an attractive pathway for obtaining a renewable fuel. By combining both the carbon fixation and ethanol generating pathways into a single organism, the costs associated with plant growth/harvesting/processing are circumvented, reducing total input energy, and increasing net energy gain. In contrast to biomass ethanol production processes, the disclosed methods will directly utilize large quantities of $CO_2$ as a carbon source for fuel production and will thus help reduce this greenhouse gas from the atmosphere.

There are numerous benefits from producing ethanol using photosynthetic microorganisms such as *Synechocystis*, including: economic opportunities for biofuel production, positive environmental impacts, reduction in global warming, and improved food security. The present methods for producing ethanol from solar energy and $CO_2$ using cyanobacteria offer significant savings in both capital and operation costs, in comparison to the biomass-based ethanol production facilities. The decreased expenditure is achieved by factors such as: simplified production processes, absence of agricultural crops and residues, no solid wastes to be treated, no enzymes needed, etc. The cyanobacteria fermentation involves no hard cellulose or hemicellulose which is difficult to treat. As a result, there will be no emissions of hazardous air pollutants and volatile organic compounds from cyanobacterial ethanol production plants.

In comparison to traditional methods for biomass ethanol production, the disclosed methods and systems will help preserve agricultural space for food production. Furthermore, cyanobacterial ethanol production plants can be highly distributed without geographical limits because they do not require grain transportation to certain locations or pretreatment of the raw material. The infrastructure and equipment required for ethanol production using the presently disclosed systems are projected to be significantly less than those required for current yeast fermentation technology, allowing for smoother integration with fuel transportation and distribution platforms.

The initial product of photosynthetic fixation of carbon dioxide is 3-phosphoglycerate. 3-phosphoglycerate is used in the Calvin Cycle to regenerate ribulose-1,5-biphosphate, which is the acceptor of carbon dioxide. There are two major branching points where the intermediates of the Calvin Cycle are connected to other metabolic pathways. At one point, fructose-6-phosphate is converted into glucose-6-phosphate and glucose-phosphate, which are the substrates for the pentose phosphate pathway, the synthesis of cellulose (a major component of the cell wall) and the synthesis of glycogen (the major form of carbohydrate reserve). At the other branching point, 3-phosphoglycerate is converted into 2-phosphoglycerate, phosphoenolpyruvate and pyruvate in a sequence of reactions catalysed by phosphoglycerate mutase, enolase and pyruvate kinase, respectively. Pyruvate is directed to the partial TCA cycle for the synthesis of amino acids, nucleotides, etc. in aerobic conditions. Pyruvate is also the substrate for ethanol synthesis.

To convert the carbohydrate reserves into ethanol, the carbohydrate reserves must be diverted to the glycolytic pathway. The presumed pathway for carbohydrate reserve metabolism in cyanobacteria is through both the glycolytic pathway and the phosphogluconate pathway. For the purposes of ethanol formation, the glycolytic pathway is of primary importance. Although not well characterized in cyanobacteria, glycogen is presumed to be metabolized into glucose 1-phosphate by a combination of glycogen phosphorylase and a 1,6-glycosidase. Phosphoglucomutase, phosphoglucoisomerase and phosphofructokinase convert glucose 1-phosphate into a molecule of fructose 1,6-bisphosphate. This compound is cleaved by the action of aldolase and triose phosphate isomerase into two molecules of glyceraldehyde 3-phosphate. This compound is converted into pyruvate through a sequential series of reactions catalysed by glyceraldehyde 3-phosphate dehydrogenase, phosphoglycerate kinase, phosphoglycerate mutase, enolase and pyruvate kinase, respectively.

In some algae and cyanobacteria strains, a small amount of ethanol is synthesized as a fermentation product under dark and anaerobic conditions (Van der Oost et al., "Nucleotide sequence of the gene proposed to encode the small subunit of the soluble hydrogenase of the thermophilic unicellular cyanobacterium *Synechococcus* PCC 6716." *Nucleic Acids Res.* 1989 Dec. 11; 17(23):10098, incorporated herein by reference in its entirety). However, the dark-anaerobic fermentation process is generally operating at a very low level, only sufficient for the survival of the organisms under such stress conditions. The synthesis of ethanol under dark and anaerobic conditions is dependent on the degradation of glycogen reserve, as described above. Moreover, it has been found that ethanol synthesis under anaerobic conditions is totally inhibited by light. Thus, in photosynthetic microorganisms ethanol synthesis is not coupled with photosynthesis and can actually be inhibited by photosynthesis.

Therefore, it has been observed that cyanobacteria do not utilize carbon dioxide to produce ethanol. Furthermore, there are no known photosynthetic microorganisms, including genetically engineered photosynthetic microorganisms, which produce ethanol in relatively substantial amounts. A further complication is that some photosynthetic organisms have been shown to be inhibited by ethanol such that the addition of ethanol to the culture medium inhibits the expression of genes involved in photosynthesis.

In the present invention, it has been found that cyanobacteria can be successfully genetically engineered to produce a quantifiable amount of ethanol as opposed to utilizing a glycogen reserve as is done under anaerobic and dark conditions. Inorganic carbon is assimilated and is used for both cellular growth and for the production of ethanol via the insertion of the ethanol generating metabolic pathway consisting of the two aforementioned enzymes pdc and adh.

II. Definitions

Unless defined otherwise, all technical and scientific terms used herein have the meaning commonly understood by a person skilled in the art to which this invention belongs. As used herein, the following terms have the meanings ascribed to them unless specified otherwise.

"Pyruvate decarboxylase" and "pdc" refer to an enzyme that catalyzes the decarboxylation of pyruvic acid to acetaldehyde and carbon dioxide. A "pdc gene" refers to the gene encoding an enzyme that catalyzes the decarboxylation of pyruvic acid to acetaldehyde and carbon dioxide. "Alcohol dehydrogenase" and "adh" refer to an enzyme that facilitates the interconversion between alcohols and aldehydes or ketones. An "adh gene" refers to the gene encoding an enzyme that facilitates the interconversion between alcohols and aldehydes or ketones. "pdc/adh" refers to the pdc and adh enzymes collectively. A "pdc/adh cassette" refers to a nucleic acid sequence encoding a pdc enzyme and an adh enzyme.

A "promoter" is an array of nucleic acid control sequences that direct transcription of an associated polynucleotide, which may be a heterologous or native polynucleotide. A promoter includes nucleic acid sequences near the start site of transcription, such as a polymerase binding site. The promoter also optionally includes distal enhancer or repressor elements which can be located as much as several thousand base pairs from the start site of transcription.

A "light responsive promoter" refers to a promoter which is responsive to light.

"Polynucleotide" and "nucleic acid" refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent crossover events. Equivalent crossing over occurs between two equivalent sequences or chromosome regions, whereas non-equivalent crossing over occurs between identical (or substantially identical) segments of nonequivalent sequences or chromosome regions. Unequal crossing over typically results in gene duplications and deletions. For a description of the enzymes and mechanisms involved in homologous recombination see, Watson et al., Molecular Biology of the Gene pp 313-327, The Benjamin/Cummings Publishing Co. 4th ed. (1987).

The term "non-homologous or random integration" refers to any process by which DNA is integrated into the genome that does not involve homologous recombination. It appears to be a random process in which incorporation can occur at any of a large number of genomic locations.

A "heterologous polynucleotide sequence" or a "heterologous nucleic acid" is a relative term referring to a polynucleotide that is functionally related to another polynucleotide, such as a promoter sequence, in a manner so that the two polynucleotide sequences are not arranged in the same relationship to each other as in nature. Heterologous polynucleotide sequences include, e.g., a promoter operably linked to a heterologous nucleic acid, and a polynucleotide including its native promoter that is inserted into a heterologous vector for transformation into a recombinant host cell. Heterologous polynucleotide sequences are considered "exogenous" because they are introduced to the host cell via transformation techniques. However, the heterologous polynucleotide can originate from a foreign source or from the same source. Modification of the heterologous polynucleotide sequence may occur, e.g., by treating the polynucleotide with a restriction enzyme to generate a polynucleotide sequence that can be operably linked to a regulatory element. Modification can also occur by techniques such as site-directed mutagenesis.

The term "expressed endogenously" refers to polynucleotides that are native to the host cell and are naturally expressed in the host cell.

An "expression cassette" or "construct" refers to a series of polynucleotide elements that permit transcription of a gene in a host cell. Typically, the expression cassette includes a promoter and a heterologous or native polynucleotide sequence that is transcribed. Expression cassettes or constructs may also include, e.g., transcription termination signals, polyadenylation signals, and enhancer elements.

The term "operably linked" refers to a functional relationship between two parts in which the activity of one part (e.g., the ability to regulate transcription) results in an action on the other part (e.g., transcription of the sequence). Thus, a polynucleotide is "operably linked to a promoter" when there is a functional linkage between a polynucleotide expression control sequence (such as a promoter or other transcription regulation sequences) and a second polynucleotide sequence (e.g., a native or a heterologous polynucleotide), where the expression control sequence directs transcription of the polynucleotide.

"Competent to express" refers to a host cell that provides a sufficient cellular environment for expression of endogenous and/or exogenous polynucleotides.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

III. Description of Embodiments

Nucleic acids and recombinant expression vectors for the optimization of ethanol production are disclosed in accordance with some embodiments of the present invention. FIG. 1 shows one embodiment of a system, described more fully in Example 1 below, that can be used to perform a variety of methods or procedures. The sequence of the pMota recombinant expression vector for optimization of ethanol production is shown in SEQ ID NO: 1. The pMota vector contains the sequences for the *Synechocystis* psbAII promoter in a 500 base pair homologous upstream region nucleic acid sequence (SEQ ID NO: 2), the nucleic acid sequence encoding *Zymomonas mobilis* pdc from PLOI295 (SEQ ID NO: 3), and the nucleic acid sequence encoding *Zymomonas mobilis* adhII from PLOI295 (SEQ ID NO: 4). The pMota vector was created by subcloning the pdc/adh cassette from PLOI295 (FIG. 1b) into the pPSBAIIKS plasmid (FIG. 1a). The pMota vector was used to integrate these genes under the control of the psbAII light responsive promoter in the cyanobacterial genome.

A recombinant expression vector for transformation of a host cell and subsequent integration of the gene(s) of interest is prepared by first isolating the constituent polynucleotide sequences, as discussed herein. In some embodiments, the gene(s) of interest are homologously integrated into the host cell genome. In other embodiments, the genes are non-homologously integrated into the host cell genome. Preferably, the gene(s) of interest are homologously integrated into the *Synechocystis* genome. In some embodiments, the pMota vector integrates into the psbAII locus via double homologous recombination. The polynucleotide sequences, e.g., a sequence encoding the pdc/adh enzymes driven by a promoter, are then ligated to create a recombinant expression vector, also referred to as a "pdc/adh construct," suitable for transformation of a host cell. Methods for isolating and preparing recombinant polynucleotides are well known to those skilled in the art. Sambrook et al., Molecular Cloning. A Laboratory Manual (2d ed. 1989); Ausubel et al., Current Protocols in Molecular Biology (1995)), provide information sufficient to direct persons of skill through many cloning exercises.

One preferred method for obtaining specific polynucleotides combines the use of synthetic oligonucleotide primers with polymerase extension or ligation on a mRNA or DNA template. Such a method, e.g., RT, PCR, or LCR, amplifies the desired nucleotide sequence (see U.S. Pat. Nos. 4,683,195 and 4,683,202). Restriction endonuclease sites can be incorporated into the primers. Amplified polynucleotides are purified and ligated to form an expression cassette. Alterations in the natural gene sequence can be introduced by techniques such as in vitro mutagenesis and PCR using primers that have been designed to incorporate appropriate mutations. Another preferred method of isolating polynucleotide sequences uses known restriction endonuclease sites to isolate nucleic acid fragments from plasmids. The genes of interest can also be isolated by one of skill in the art using primers based on the known gene sequence.

Promoters suitable for the present invention include any suitable light-responsive promoter such as, for example, the psbAII promoter and the nirA promoter. In some embodiments, the promoter is the in situ native psbAII promoter that, in wild type *Synechocystis* sp. PCC 6803 cells, mediates the transcription of the psbAII gene that encodes the D1 subunit of photosystem II. The psbAII light responsive promoter is located immediately upstream of the endogenous psbAII gene in *Synechocystis* sp PCC 6803. In some embodiments, the promoter is the nirA promoter, which is a 166 base pair *Synechococcus* sp. strain PCC 7942 promoter sequence described by Qi et al. (2005) in development of an inducible expression vector for *Synechocystis* sp. PCC 6803.

In some embodiments, the promoter comprises the nucleic acid sequence shown in SEQ ID NO: 2, which contains the psbAII promoter. In some embodiments, the promoter comprises the nucleic acid sequence shown in SEQ ID NO: 5. In other embodiments, the promoter comprises the *Synechococcus* nirA promoter sequence shown in SEQ ID NO: 6. In SEQ ID NO: 6, the TCC at the 3' terminus of the wild type nirA promoter was replaced with the sequence CAT in order to generate an NdeI restriction site at the start codon while maintaining the spatial integrity of the promoter/ORF construct. This allows for the creation of a system whereby the gene(s) of interest may be expressed via induction by addition of nitrate to the culture media. Ammonia may be used as the nitrogen source for growth prior to induction. (Qi et al., 2005). In some embodiments, a 500 base pair homologous upstream region containing the psbAII promoter having the sequence shown in SEQ ID NO: 2 is used in constructing the recombinant expression vector. The 500 base pair homology targets the vector for integration into the psbAII locus via double homologous recombination.

Any pdc gene capable of being expressed may be used in the present invention. In some embodiments, the pdc gene is the *Zymomonas mobilis* pdc gene. In some embodiments, the pdc gene is obtained from the *Zymomonas mobilis* plasmid pLOI295. In some embodiments, the pdc gene comprises the nucleic acid sequence shown in SEQ ID NO: 3. In some embodiments, the pdc gene is a nucleic acid sequence encoding the protein shown in SEQ ID NO: 7. In other embodiments, the pdc gene is a nucleic acid encoding the pdc enzyme obtained from *Zymobacter palmae*. The NCBI accession number for the complete pdc protein sequence from *Zymobacter palmae* is AF474145 (SEQ ID NO: 8). In some embodiments, the pdc gene is a nucleic acid sequence encoding the amino acid sequence shown in SEQ ID NO: 8. There are other sources of pdc and adh enzymes, including *Saccharomyces cerevisciae*.

Any adh gene capable of being expressed may be used in the present invention. In some embodiments, the adh gene is the *Zymomonas mobilis* adhII gene. In some embodiments, the adh gene is obtained from the *Zymomonas mobilis* plasmid pLOI295. In some embodiments, the adh gene comprises the nucleic acid sequence shown in SEQ ID NO: 4. In some embodiments, the pdc gene is a nucleic acid sequence encoding the amino acid sequence shown in SEQ ID NO: 9.

The isolated polynucleotide sequence of choice, e.g., the pdc/adh genes driven by the promoter sequence discussed above, is inserted into an "expression vector," "cloning vector," or "vector," terms which usually refer to plasmids or other nucleic acid molecules that are able to replicate in a chosen host cell. Expression vectors can replicate autonomously, or they can replicate by being inserted into the genome of the host cell.

Often, it is desirable for a vector to be usable in more than one host cell, e.g., in *E. coli* for cloning and construction, and in, e.g., *Synechocystis* for expression. Additional elements of the vector can include, for example, selectable markers, e.g., kanamycin resistance or ampicillin resistance, which permit detection and/or selection of those cells transformed with the desired polynucleotide sequences.

The particular vector used to transport the genetic information into the cell is also not particularly critical. Any suitable vector used for expression of recombinant proteins can be used. In preferred embodiments, a vector that is capable of being inserted into the genome of the host cell is used. In some embodiments, the vector is pSBAIIKS, created and described by Lagarde et al. (2000). Expression vectors typically have an expression cassette that contains all the elements required for the expression of the polynucleotide of choice in a host cell. A typical expression cassette contains a promoter operably linked to the polynucleotide sequence of choice. The promoter used to direct expression of pdc/adh is as described above, and is operably linked to a sequence encoding the pdc/adh proteins. The promoter is preferably positioned about the same distance from the heterologous transcription start site as it is from the transcription start site in its natural setting. As is known in the art, however, some variation in this distance can be accommodated without loss of promoter function.

In addition to the pdc/adh genes, the expression vector for the optimization of ethanol production may include genes for the tolerance of a host cell to economically relevant ethanol concentrations. For example, genes such as omrA, lmrA, and lmrCD may be included in the expression vector. OmrA from wine lactic acid bacteria *Oenococcus oeni* and its homolog LmrA from *Lactococcus lactis* have been shown to increase the relative resistance of tolC(−) *E. Coli* by 100 to 10,000 times. (Bourdineaud et al., 2004) Therefore, it may be beneficial to incorporate omrA, lmrA, and other homologues in order to increase the ethanol tolerance of a host cell. In some embodiments, the expression vector comprising the pdc/adh genes further comprises the omrA gene. In other embodiments, the expression vector comprising the pdc/adh genes further comprises the lmrA gene. In other embodiments, the expression vector comprising the pdc/adh genes further comprises the lmrCD gene. Any promoters suitable for driving the expression of a heterologous gene in a host cell can be used to drive the genes for the tolerance of a host cell, including those typically used in standard expression cassettes.

After construction and isolation of the recombinant expression vector, it is used to transform a host cell for ethanol production. The particular procedure used to introduce the genetic material into the host cell for expression of a protein is not particularly critical. Any of the well known procedures for introducing foreign polynucleotide sequences into host cells can be used. In some embodiments, the host cells can be transformed and screened sequentially via the protocol described by Williams (1988). This method exploits the natural transformability of the *Synechocystis* sp. PCC 6803 cyanobacteria, where transformation is possible via simple incubation of purified plasmid construct with exponentially growing cells.

Host cells for transformation with the recombinant expression vector described above include any suitable host cyanobacterium competent to produce ethanol, especially members of the genus *Synechocystis*. Host cells suitable for use in the present invention include, for example, wild type *Synechocystis* sp. PCC 6803 and a mutant *Synechocystis* created by Howitt et al. (1999) that lacks a functional NDH type 2 dehydrogenase (NDH-2(−)). The type 2 dehydrogenase is specific for the regeneration of NAD+ from NADH. Flux through the ethanol pathway may be increased in the mutant. In particularly preferred embodiments, the host cells are *Synechocystis*. Host cells that are transformed with the pdc/adh construct are useful recombinant cyanobacteria for production of ethanol. Preferred subspecies of *Synechocystis* include, e.g., *Synechocystis* PCC 6803. A preferred strain is the *Synechocystis* sp. PCC 6803 NDH-2(−) mutant.

After the host cell is transformed with the pdc/adh construct, the host cell is incubated under conditions suitable for production of ethanol. Typically, the host cell will be grown in a photoautotrophic liquid culture in BG-11 media, with a 1 L/min air sparge rate and a pH setpoint of 8.5, controlled via sparging with $CO_2$, and the temperature maintained at 30° C. Various media for growing cyanobacteria are known in the art. In some embodiments, *Synechocystis* sp. PCC 6803 is cultured on standard BG-11 media plates, with or without the addition of (final concentration): 5 mM glucose, 5% sucrose, and/or either 5 µg ml$^{-1}$, 25 µg ml$^{-1}$, or 50 µg ml$^{-1}$ kanamycin. Plates containing *Synechocystis* sp. PCC 6803 were incubated at 30° C. under ~100 microeinsteins m$^2$ s$^{-1}$. All *Synechocystis* liquid cultures were grown in standard BG-11, with the addition of 50 µg ml$^{-1}$ kanamycin when appropriate.

Enhanced secretion of ethanol is observed after host cells competent to produce ethanol are transformed with the pdc/adh construct and the cells are grown under suitable conditions as described above. Enhanced secretion of ethanol may be observed by standard methods, discussed more fully below in the Examples, known to those skilled in the art. In some embodiments, the host cells are grown using batch cultures. In some embodiments, the host cells are grown using photobioreacter fermentation. In some embodiments, the host cells are grown in a BIOFLO® Reactor. In some embodiments, the growth medium in which the host cells are grown is changed, thereby allowing increased levels of ethanol production. The number of medium changes may vary. Ethanol concentration levels may reach from about 5 mM to about 15 mM after about 2 to about 5 days of fermentation. In cases where the medium is changed, ethanol concentration levels may reach from about 25 to about 100 mM after 5 days of fermentation. In some embodiments, the ethanol production level is about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9 or 15.0 mM after about 5 days of fermentation. In cases where the medium is changed, in some embodiments, the ethanol production level is about 25.0, 25.1, 25.2, 25.3, 25.4, 25.5, 25.6, 25.7, 25.8, 25.9, 26.0, 26.1, 26.2, 26.3, 26.5, 26.6, 26.7, 26.8, 26.9, 27.0, 27.1, 27.2, 27.3, 27.5, 27.6, 27.7, 27.8, 27.9, 28.2, 28.2, 28.3, 28.5, 28.6, 28.7, 28.8, 28.9, 29.0, 29.1, 29.2, 29.3, 29.5, 29.6, 29.7, 29.8, 29.9, 30.0, 30.1, 30.2, 30.3, 30.4, 30.5, 30.6, 30.7, 30.8, 30.9, 31.0, 31.1, 31.2, 31.3, 31.4, 31.5, 31.6, 31.7, 31.8, 31.9, 32.0, 32.1, 32.2, 32.3, 32.4, 32.5, 32.6, 32.7, 32.8, 32.9, 33.0, 33.1, 33.2, 33.3, 33.4, 33.5, 33.6, 33.7, 33.8, 33.9, 34.0, 34.1, 34.2, 34.3, 34.4, 34.5, 34.6, 34.7, 34.8, 34.9, 35.0, 35.1, 35.2, 35.3, 35.4, 35.5, 35.6, 35.7, 35.8, 35.9, 36.0, 36.1, 36.2, 36.3, 36.5, 36.6, 36.7, 36.8, 36.9, 37.0, 37.1, 37.2, 37.3, 37.5, 37.6, 37.7, 37.8, 37.9, 38.2, 38.2, 38.3, 38.5, 38.6, 38.7, 38.8, 38.9, 39.0, 39.1, 39.2, 39.3, 39.5, 39.6, 39.7, 39.8, 39.9, 40.0, 40.1, 40.2, 40.3, 40.4, 40.5, 40.6, 40.7, 40.8, 40.9, 41.0, 41.1, 41.2, 41.3, 41.4, 41.5, 41.6, 41.7, 41.8, 41.9, 42.0, 42.1, 42.2, 42.3, 42.4, 42.5, 42.6, 42.7, 42.8, 42.9, 43.0, 43.1, 43.2, 43.3, 43.4, 43.5, 43.6, 43.7, 43.8, 43.9, 44.0, 44.1, 44.2, 44.3, 44.4, 44.5, 44.6, 44.7, 44.8, 44.9, 45.0, 45.1, 45.2, 45.3, 45.4, 45.5, 45.6, 45.7, 45.8, 45.9, 46.0, 46.1, 46.2, 46.3, 46.5, 46.6, 46.7, 46.8, 46.9, 47.0, 47.1, 47.2, 47.3, 47.5, 47.6, 47.7, 47.8, 47.9, 48.2, 48.2, 48.3, 48.5, 48.6, 48.7, 48.8, 48.9, 49.0, 49.1, 49.2, 49.3, 49.5, 49.6, 49.7, 49.8, 49.9 or 50.0 mM after about 5 days of fermentation. The fermentation times may vary from about 2 days to about 30 days of fermentation. In some embodiments, the fermentation time is about 2, 3, 4, 5, 6, 7, 8, 9, 10, 11, 12, 13, 14, 15, 16, 17, 18, 19, 20, 21, 22, 23, 24 or 25 days.

The air sparge rate during host cell growth may be from 0.1 L/min to 3.0 L/min. In some embodiments, the air sparge rate during host cell growth is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 L/min. Preferably, the air sparge rate is L/min. The pH setpoint for host cell growth may be from 7.0 to 9.5. In some embodiments, the pH setpoint is about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, or 9.5. The temperature during host cell growth may be from about 25° C. to 35° C. In some embodiments, the temperature is about 25.0, 25.1, 25.2, 25.3, 25.4, 25.5, 25.6, 25.7, 25.8, 25.9, 26.0, 26.1, 26.2, 26.3, 26.5, 26.6, 26.7, 26.8, 26.9, 27.0, 27.1, 27.2, 27.3, 27.5, 27.6, 27.7, 27.8, 27.9, 28.2, 28.2, 28.3, 28.5, 28.6, 28.7, 28.8, 28.9, 29.0, 29.1, 29.2, 29.3, 29.5, 29.6, 29.7, 29.8, 29.9, 30.0, 30.1, 30.2, 30.3, 30.4, 30.5, 30.6, 30.7, 30.8, 30.9, 31.0, 31.1, 31.2, 31.3, 31.4, 31.5, 31.6, 31.7, 31.8, 31.9, 32.0, 32.1, 32.2, 32.3, 32.4, 32.5, 32.6, 32.7, 32.8, 32.9, 33.0, 33.1, 33.2, 33.3, 33.4, 33.5, 33.6, 33.7, 33.8, 33.9, 34.0, 34.1, 34.2, 34.3, 34.4, 34.5, 34.6, 34.7, 34.8, 34.9 or 35.0° C.

The following examples are by way of illustration and not by way of limitation.

Example 1

Creation of the Transformation Vector, pMota

This Example illustrates the preparation of the transformation vector, pMota.

PCR was used for amplification of the pdc/adhII cassette from pLOI295 and for the simultaneous introduction of NdeI and BamHI sites at the 5' and 3' ends, respectively. These sites then allowed for subcloning pdc/adhII into the backbone of the pPSBAIIKS plasmid, resulting from removal of the aphX/sacB selection cassette via NdeI/BamHI dual digestion, yielding pMota. The following primers were used for the above PCR reaction (restriction sites are underlined, induced mutations are in bold: Upstream: 5'-ggAgTAAgCATATgAgTTATACTg-3' (SEQ ID NO: 10) Downstream: 5'-ggATCTCgACTCTAgAggATCC-3' (SEQ ID NO: 11). PCR was carried out as follows: Total reaction vol. of 50 µl, 0.36 µg of pLOI295 as template, 4 Units of Vent$_R$® polymerase, a final concentration of 0.5 µM for each primer, 300 µM of each dNTP. The reaction was run on the following program on an Eppendorf® Mastercycler®: Initial denaturation at 94° C. for 2 min, followed by 35 cycles of 10 s denaturation at 94° C., 1 min annealing at 47° C., and 3.7 min extension at 68° C.; finally, hold at 4° C.

All plasmid/PCR product cleanup kits and Taq DNA polymerase were acquired from Qiagen®. All restriction enzymes, Vent$_R$® Polymerase and T4 DNA ligase were obtained from New England Biolabs®. Plasmid PSBAIIKS was obtained from Wim F. J. Vermaas at Arizona State University. Plasmid LOI295, containing the *Z. mobilis* pdc and adhII genes, was obtained from Lonnie O. Ingram at the University of Florida.

Example 2

Transformation and Screening for Stable Ethanol Production

This Example illustrates the construction of a stable cyanobacteria line for production of ethanol.

Following creation of pMota (see Example 1 above), both wild type and NDH-2(−) mutant strains of *Synechocystis* sp. PCC 6803 were transformed and screened sequentially with pPSBAIIKS and pMota via the protocol described by Williams (1988). After transformation with pPSBAIIKS, serial replating on increasing kanamycin concentrations allowed for the isolation of strains WT$_{[r]}$ and NDH-2(−)$_{[r]}$, completely segregated with respect to the aphX/sacB selection cassette, as verified by a PCR based assay. These in turn were grown in liquid seed culture, under the presence of 50 µg ml$^{-1}$ kanamycin, and subsequently transformed with pMota.

Transformants were screened on BG-11 plates containing 5% sucrose. Screening was performed via serial streaking of single colonies coupled with both an initial PCR based assay used for probing the psbAII loci and finally a seed reactor based assay for determination of stability of ethanol generation given the absence of selective pressure. The PCR assay consisted of three PCR reactions per sample, probing for the presence of the (1) WT psbAII gene, (2) aphX/sacB selection cassette, and (3) pdc/adhII ethanol pathway cassette. Each of the three reactions comprising the PCR assay shared a common upstream primer that lies outside of the psbAII gene loci, while each reaction is defined by the downstream primer that is specific for each of the three possible genetic constructs. The upstream primer used in all three reactions was: 5'-gTCAgTTCCAATCTAACATCGA-3' (SEQ ID NO: 12), with the amplicon beginning 48 bp upstream of the psbAII start codon. The downstream primer for probing the WT psbAII gene: 5'-AATTTgTAACCgTAgTTCTgggAT-3' (SEQ ID NO: 13), and the resultant amplicon is 749 bp. For probing the aphX/sacB selection cassette, downstream primer: 5'-TTggT-gATTTTgAACTTTFgCTTgC-3' (SEQ ID NO: 14), was used, resulting in a 3.1 kb amplicon. The downstream primer for probing the pdc/adhII cassette: 5'-TTgCAAgCgATTTCg-gATAAA-3' (SEQ ID NO: 15), resulting in a 554 bp amplicon. All PCR reactions were formulated as described in the Qiagen® Taq Polymerase Handbook in the section for long PCR products, modified only by the exclusion of any high fidelity polymerase. The PCR assay utilized the following cycling program: Initial denaturation at 94° C. for 3 min, followed by 35 cycles of 10 s denaturation at 94° C., 1 min annealing at 48° C., and 3.5 min extension at 68° C.; a final 3 min extension at 68° C., hold at 4° C.

To perform the PCR assay on a given cyanobacterial sample, Whatman® brand FTA® cards were used for rapid preparation of genomic DNA for use as a template in the above PCR reaction. For testing a liquid culture, 5 µl was spotted onto the FTA® card. For testing cultures streaked on solid media, multiple colonies were lifted from the plate, streaked on the inside of a 1.5 ml tube and resuspended in 10 µl of BG-11 via vortexing; 5 µl were then spotted onto the FTA® card, as above. The FTA® protocol for preparation of the archived DNA from a bacterial source was followed for preparation of the template for the PCR assay.

The primary seed reactor based assay was used to screen colonies that were shown to be completely segregated for the ethanol cassette for stable ethanol production. Seed reactors were inoculated with multiple colonies from a plate of a given isolate. The cells were grown to an OD$_{730}$ of greater than 0.1, centrifuged at 3220×g for 6 min at room temperature, and resuspended in a fresh seed reactor at an initial OD$_{730}$=0.025 This constituted the first experimental reactor in a series of five runs. The reactor was run for five days, at which point the cells were again collected by centrifugation and used to inoculate the second experimental reactor in the series to the above OD$_{730}$=0.025. Of course, only a subset of the total cell biomass were used for this serial inoculation while the rest were discarded or glycerol stocked. Each day of a particular run, the OD$_{730}$ were recorded, and a 550 µl aliquot were taken for ethanol concentration assay (the 'before' aliquot). The cells were then washed by collection via centrifugation (as above), discarding the supernatant, resuspension by vortexing of the entire pellet in 25 ml of fresh BG-11, and returned to the seed reactor. The OD$_{730}$ were again recorded and another aliquot was taken for ethanol concentration assay (the so called 'after' aliquot). After isolation of a stable ethanol producing isolate, the PCR based assay was applied a final time for complete confirmation.

Wild Type (WT) *Synechocystis* sp. strain PCC 6803 and the NDH-2(−) mutant, lacking any functional NADH-oxidizing type II dehydrogenase, were obtained from Wim F. J. Vermaas at Arizona State University. C600 *E. coli* were obtained from the laboratory of Monto Kumagai, while at the University of Hawaii at Manoa.

*E. coli* was cultured on standard LB formulation in both liquid and solid media. Ampicillin and kanamycin were supplemented to the LB media plates at concentrations of 100 µg ml$^{-1}$ and 50 µg ml$^{-1}$, respectively.

All *Synechocystis*-sp. PCC 6803 was cultured on standard BG-11 media plates, with or without the addition of (final concentration): 5 mM glucose, 5% sucrose, and/or either 5 µg ml$^{-1}$, 25 µg ml$^{-1}$, or 50 µg ml$^{-1}$ kanamycin. Plates containing *Synechocystis* sp. PCC 6803 were incubated at 30° C. under ~100 microeinsteins m$^{-2}$ s$^{-1}$. All *Synechocystis* liquid cultures were grown in standard BG-11, with the addition of 50 µg ml$^{-1}$ kanamycin when appropriate.

Example 3

Batch Growth Experiments

This Example illustrates batch growth experiments for productivity and stability studies.

A parallel batch culture system (six 100 mL bioreactors) was established to grow the ethanol-producing *Synechocystis* strains developed. Standard BG-11 liquid media was used for the all the experiments. Agitation was set at 400 rpm. Lighting intensity was 200 microeinsteins on the formost face of the bioreactors. Compressed air was sparged to provide $CO_2$ and remove the oxygen produced by *Synechocystis*. Semi batch operation mode was used to test the ethanol production. The total cell growth period was 20 days. The seed cultures were started from a plate. Exponentially growing cells from a seed culture were inoculated into the reactors at $OD_{730}$=0.025. Batch cultures were conducted for about 4 days, and then terminated. The cells were spun down by centrifugation, resuspended in a reduced volume, and an aliquot was used to inoculate a bioreactor with fresh media.

Example 4

Ethanol Concentration Assay

This Example illustrates determination of the ethanol concentration in a liquid culture.

For determination of ethanol concentration of a liquid culture, a 550 µl aliquot of the culture was taken, spun down at 12,100×g for 5 min, and 500 µl (or other appropriate vol.) of the supernatant was placed in a fresh 1.5 ml tube and stored at −20° C. until performing the assay. Given the linear range of the spectrophotometer and the sensitivity of the ethanol assay, dilution of the sample (up to 20 fold) was occasionally required. In this case, an appropriate volume of BG-11 was first added to the fresh 1.5 ml tube, to which the required vol. of clarified supernatant was added. This solution was used directly in the ethanol assay. Upon removal from −20° C. and immediately before performing the assay, the samples were spun down a second time at 12,100×g for 5 min, also assisting in sample thawing.

The Boehringer Mannheim/r-Biopharm® enzymatic ethanol detection kit was used for ethanol concentration determination. Briefly, this assay exploits the action of alcohol dehydrogenase (ADH) and acetaldehyde dehydrogenase in a phosphate-buffered solution of the $NAD^+$ cofactor, which upon the addition of ethanol causes a conversion of $NAD^+$ to NADH. Concentration of NADH is determined by light absorbance at 340 nm ($A_{340}$) and is then used to determine ethanol concentration. The assay was performed as given in the instructions, with the following modifications. As given under point 4 on the instruction sheet, the maximal sample volume (v=0.5 ml), for maximum sensitivity, was used for the assay. Finally, all volumes in the assay (including the above v=0.5 ml) were quartered. This allowed for reagent conservation, and the ability to retain a majority of the sample aliquot's volume, in case repetition was required. Thus, the sample volume used was actually v=0.125 ml, in 0.75 ml of reaction mixture 2, and with the later addition of 12.5 µl of (ADH) suspension 3. This conserved ratio volumetric reduction was determined to have no effect on the assay as performed. BG-11 was used as a blank.

Example 5

Autotrophic Photobioreactor Fermentation

This Example illustrates production of ethanol using autotrophic photobioreactor fermentation.

Liquid seed cultures were grown at 24° C. in an incubating shaker (Innova 4230 benchtop, New Brunswick) with a light which possesses a maximal surface flux of ~200 microeinsteins m$^{-2}$ s$^{-1}$ on the seed reactor face, agitated via magnetic stir bar, and sparged with compressed air at a rate of approximately 0.5 L/min. Primary seed cultures consisted of a total volume of 25 ml in a standard 100 ml Pyrex™ media bottle, with a two Pasteur pipettes serving as the sparge and the offgas tubes. Upstream of the sparge tube was a Whatman® PFTE 0.1 µm filter and the offgas tube was loosely capped with aluminum foil. The secondary seed culture used for photobioreactor inoculation was identical to the primary seed culture, except the culture volume was 300 ml grown in a standard 1 L Pyrex™ media bottle, the sparging pipette was replaced with a level C porosity diffuser, pore size 25-50 µm, from Ace Glass Inc. Lights used were 40 W cool white fluorescent tubes. Cell growth in liquid culture was monitored by determination of optical density at 730 nm ($OD_{730}$) using a ThermoSpectronic® Genesys® 10-S Spectrophotometer. Plastibrand® UltraVette® 1.5 ml disposable cuvettes were used.

Exponentially growing seed culture from primary seed reactors were used to inoculate a secondary seed reactor, which was then grown to an $OD_{730}$>0.31 and immediately used for inoculation of the autotrophic photobioractor. For inoculation, the $OD_{730}$ was taken and used for determination of the seed culture volume required for initial bioreactor $OD_{730}$=0.02 (total fermentation vol. was 3.1 L). Cells from this determined volume of seed culture were harvested via centrifugation and resuspended in 50 ml of fresh BG-11 by vortexing. After inoculation of the bioreactor with this 50 ml seed, an additional 50 ml of BG-11 was used for flushing of the inoculation tube.

Figure 2:
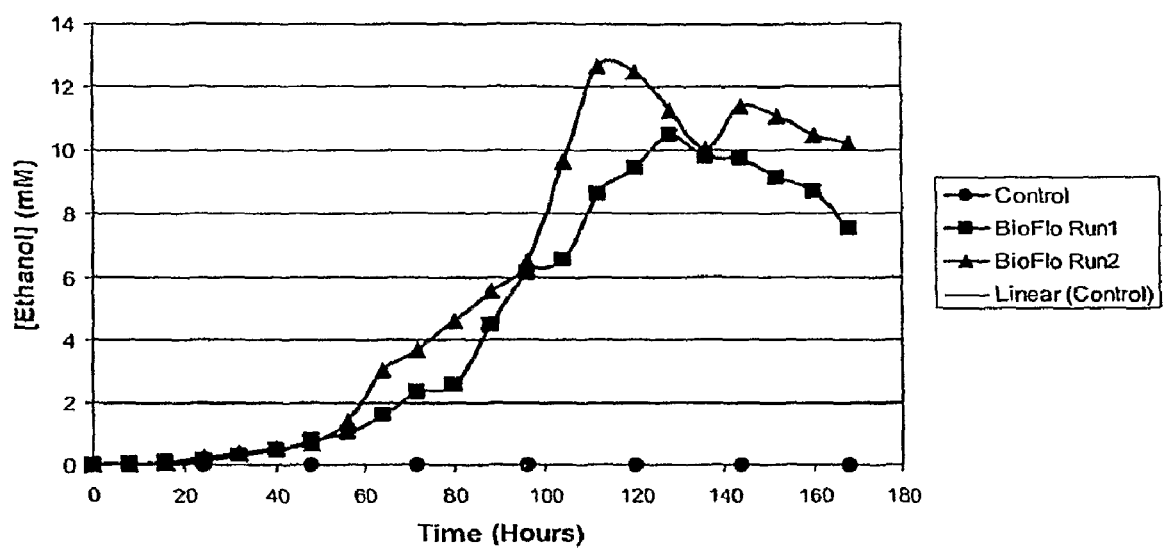
FIG. 2 shows ethanol concentration vs. time in the BIO-FLO® Reactor. Ethanol concentration reached 13 mM after five days of fermentation. The control is non-transformed (wild-type) *Synechocystis*.

A 7.5 L BIOFLO® 110 bioreactor system (New Brunswick Scientific, Edison, N.J.) was used for the experiments. The 7.5 L BIOFLO® 110 bioreactor system includes controllers for temperature, pH and dissolved oxygen concentration (DO) adjustment. The *Synechocystis* cultivation process was monitored and controlled automatically by a Pentium® II (233 MHz, Windows 98) computer equipped with an interface board PCI-MIO-16E-10 (National Instruments Corp., Austin, Tex.). The data acquisition program was written in LabVIEW7.1 (National Instruments Corp., Austin, Tex.). The data from the BIOFLO® 110 bioreactor system, including pH, agitation, temperature and DO were acquired through the computer interface board. Six General Electric® 26 W, F26DBX/SPX41/4P bulbs were arrayed around the reactor to give a maximal surface flux of ~1000 microeinsteins m$^{-2}$ S$^{-1}$ on the reactor surface. The reactor was maintained at 27-29° C. throughout the fermentation via an external fan circulating air around the lighting system. The reactor was sparged with air at a rate of 1 L/min, the pH was controlled via $CO_2$ injection with the setpoint at 8.5, and the agitation turbine was set to 300 rpm. The condenser on the offgas port was chilled to 8° C. via a thermo circulating water bath (C10-K20, Haake, Berlin, Germany). Fermentation was maintained for eight days, with sampling every eight hours. For sampling, ~15 ml was drawn from the reactor via the sampling port (to clear the harvesting downtube), discarded, and a second ~15 ml aliquot, the sample, was drawn. From each sample $OD_{730}$ was recorded and an aliquot was taken for the ethanol concentration assay. The ethanol concentration was 12 mM after 112 hours of fermentation (FIG. 2). After 5 days of fermentation, an ethanol concentration of 13 mM was reached (FIG. 2).

The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

It will be apparent to one skilled in the art that varying substitutions and modifications can be made to the invention disclosed herein without departing from the scope and spirit of the invention.

Those skilled in the art recognize that the aspects and embodiments of the invention set forth herein can be practiced separate from each other or in conjunction with each other. Therefore, combinations of separate embodiments are within the scope of the invention as disclosed herein.

REFERENCES

Deng, M. and Coleman, J., 1999. "Ethanol Synthesis by Genetic Engineering in Cyanobacteria" *Applied and Environmental Microbiology* 65(2):523-428.

Sun, Y. and Cheng, J., 2002. "Hydrolysis of lignocellulosic material from ethanol production: A review" *Biores. Technol.*, 83:1-11.

BBI International Consulting Division, 2003. Economic Impact Assessment for Ethanol Production and Use in Hawaii. Prepared for Energy, Resources and Technology Division Department of Business, Economic Development and Tourism State of Hawaii.

United States Environmental Protection Agency (USEPA), 2000. "VOC emissions compliance study performed for new energy corporation at the fuel ethanol plant dryer exhaust stack D513, South Bend Ind." Submitted by Mostardi Plantt, December 2000.

United States Environmental Protection Agency, 2001. "Results of the Sep. 6, 2001, VOC and particulate emission compliance testing at the Agri-Energy facility located in Luverne, Minn." submitted Environmental resource group. October 2001.

United States Environmental Protection Agency, 2002a. "VOC emission test results, feed dryer 1-5: super stack/ RTO Co2 scrubber/RTO" submitted by Archer Daniels Midland Co., February 2002.

United States Environmental Protection Agency, 2002b. Headquarters Press Release, Washington D.C., "United States settles with 12 Minnesota ethanol companies", Oct. 2, 2002.

Bourdineaud et al., 2003. "The ftsH gene of the wine bacterium Oenococcus oeni is involved in protection against environmental stress." *Appl Environ Microbiol.* 69(5):2512-20.

Kaneko et al., 1996. "Sequence Analysis of the Genome of the Unicellular Cyanobacterium *Synechocystis* sp. Strain PCC6803.II. Sequence Determination of the Entire Genome and Assignment of Potential Protein-coding Regions." *DNA Res.* 3(3): 185-209.

Qi et al., 2005. "Application of the *Synechococcus* nirA Promoter To Establish an Inducible Expression System for Engineering the *Synechocystis* Tocopherol Pathway." *Appl. Environ. Microbiol.* 71(10): 5678-5684.

Lagarde et al., 2000. "Increased Production of Zeaxanthin and Other Pigments by Application of Genetic Engineering Techniques to *Synechocystis* sp. Strain PCC 6803." *Appl. Environ. Microbiol.* 66(1):64-72.

Ingram et al., 1987. "Genetic Engineering of Ethanol Production in *Escherichia coli.*" *Appl. Environ. Microbiol.* 53(1): 2420-2425.

Williams, J. G. K. 1988. "Construction of specific mutations in photosystem II reaction center by genetic engineering methods in *Synechocystis* 6803." *Methods Enzymol.* 167: 766-778.

Howitt et al., 1999. "Type 2 NADH Dehydrogenases in the Cyanobacterium *Synechocystis* sp. Strain PCC 6803 Are Involved in Regulation Rather Than Respiration." *Journal of Bacteriology* 181(13):3994-4003.

All patents and publications are herein incorporated by reference in their entireties to the same extent as if each individual publication was specifically and individually indicated to be incorporated by reference.

The invention illustratively described herein suitably can be practiced in the absence of any element or elements, limitation or limitations that is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

What is claimed is:

1. A *Synechocystis* host cell comprising a nucleic acid construct comprising: a light responsive promoter, a sequence encoding a pyruvate decarboxylase (pdc) enzyme, and a sequence encoding an alcohol dehydrogenase (adh) enzyme, wherein the cyanobacterium is wild-type or a NDH-2(−) mutant strain of *Synechocystis* sp. PCC 6803, the light responsive promoter is the psbAII promoter and the sequences encoding a pdc enzyme and an adh enzyme are obtained from the *Zymomonas mobilis* plasmid pLOI295.

2. The *Synechocystis* host cell of claim 1, wherein the sequence encoding a psbAII promoter comprises SEQ. ID NO: 2 or a gene sequence that encodes psbAII and that is capable of expression in cyanobacteria.

3. The *Synechocystis* host cell of claim 1 wherein the nucleic acid construct is an expression vector.

4. The *Synechocystis* host cell of claim 3, wherein the expression vector is a plasmid.

5. The *Synechocystis* host cell of claim 4, wherein the expression vector is pMota.

6. The *Synechocystis* host cell of claim 3, wherein the expression vector is integrated into the host cell chromosome.

7. The *Synechocystis* host cell of claim 6, wherein the expression vector is pMota.

8. The host cell of claim 6, wherein the host cell is capable of producing ethanol in relatively quantifiable amounts after a period of light exposure at a flux of about 1000 µE m$^{-2}$ s$^{-1}$.

9. The host cell of claim 6, wherein the host cell is capable of producing ethanol in recoverable quantities greater than about 10 mM ethanol after about five days of culture.

10. The host cell of claim 6, wherein the host cell is capable of producing ethanol in recoverable quantities of about 13 mM ethanol after about five days of culture.

11. A genetically engineered *Synechocystis* cyanobacterium comprising a construct comprising nucleic acid sequences encoding a light responsive promoter and encoding pyruvate decarboxylase (pdc) and alcohol dehydrogenase (adh) enzymes, wherein the cyanobacterium is wild-type or a NDH-2(−) mutant strain of *Synechocystis* sp. PCC 6803, the cyanobacterium is capable of producing ethanol in recoverable quantities greater than about 10 mM ethanol after about five days of culture, the light responsive promoter is the psbAII promoter and the nucleic acid sequences that encode pdc and adh enzymes are obtained from the *Zymomonas mobilis* plasmid pLOI295.

12. The cyanobacterium of claim 11, wherein the construct is pMota.

13. A method of producing ethanol, comprising: culturing cyanobacteria in a culture medium under inducing conditions for a light responsive promoter, the cyanobacteria containing a construct comprising DNA fragments that encode the light responsive promoter and DNA fragments obtained from the *Zymomonas mobilis* pLOI295 plasmid that encode pdc and adh enzymes, wherein the cyanobacterium is wild-type or a NDH-2(−) mutant strain of *Synechocystis* sp. PCC 6803 and the light responsive promoter is the psbAII promoter; and accumulating ethanol in the culture medium in an amount greater than about 5 mM ethanol after about five days of culture.

14. The method of claim 13, wherein the ethanol concentration of the culture medium is at least about 10 mM after about five days of culture.

15. The method of claim 13, wherein the ethanol concentration of the culture medium is at least about 13 mM after about five days of culture.

16. The method of claim 13, wherein said construct is pMota.

17. The method of claim 13, wherein the construct is integrated into the cyanobacteria chromosome.

* * * * *

UNITED STATES PATENT AND TRADEMARK OFFICE
CERTIFICATE OF CORRECTION

PATENT NO. : 8,372,613 B2  
APPLICATION NO. : 12/160770  
DATED : February 12, 2013  
INVENTOR(S) : Pencheng Patrick Fu and Jason Dexter Page 1 of 1

It is certified that error appears in the above-identified patent and that said Letters Patent is hereby corrected as shown below:

On the Title Page:

Item (73) Assignee: delete "Algenol Biofuels, Inc., Bonita Springs, FL (US)" and insert --University of Hawaii, Honolulu, HI (US)--

Signed and Sealed this  
Sixteenth Day of July, 2013

Teresa Stanek Rea  
*Acting Director of the United States Patent and Trademark Office*

SEQUENCE LISTING

```
<160> NUMBER OF SEQ ID NOS: 15

<210> SEQ ID NO 1
<211> LENGTH: 7286
<212> TYPE: DNA
<213> ORGANISM: Artificial Sequence
```

<220> FEATURE:
<223> OTHER INFORMATION: Recombinant expression vector pMota

<400> SEQUENCE: 1

```
tcttccgctt cctcgctcac tgactcgctg cgctcggtcg ttcggctgcg gcgagcggta      60
tcagctcact caaaggcggt aatacggtta tccacagaat caggggataa cgcaggaaag     120
aacatgtgag caaaaggcca gcaaaaggcc aggaaccgta aaaaggccgc gttgctggcg     180
ttttttccata ggctccgccc ccctgacgag catcacaaaa atcgacgctc aagtcagagg    240
tggcgaaacc cgacaggact ataaagatac caggcgtttc ccctggaag ctccctcgtg     300
cgctctcctg ttccgaccct gccgcttacc ggatacctgt ccgcctttct ccttcggga    360
agcgtggcgc tttctcatag ctcacgctgt aggtatctca gttcggtgta ggtcgttcgc    420
tccaagctgg gctgtgtgca cgaaccccccc gttcagcccg accgctgcgc cttatccggt   480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aagaacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga taaggcgga cacggaaatg ttgaatactc   1800
atactcttcc ttttttcaata ttattgaagc atttatcagg gttattgtct catgagcgga  1860
tacatatttg aatgtattta gaaaaataaa caaataggg ttccgcgcac atttccccga    1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccataaa attgtaaacg ttaatatttt gttaaaattc   2220
gcgttaaatt tttgttaaat cagctcattt tttaaccaat aggccgaaat cggcaaaatc   2280
```

```
ccttataaat caaaagaata gcccgagata gggttgagtg ttgttccagt ttggaacaag   2340
agtccactat taaagaacgt ggactccaac gtcaaagggc gaaaaaccgt ctatcagggc   2400
gatggcccac tacgtgaacc atcacccaaa tcaagttttt tggggtcgag gtgccgtaaa   2460
gcactaaatc ggaaccctaa agggagcccc cgatttagag cttgacgggg aaagccggcg   2520
aacgtggcga aaaggaagg gaagaaagcg aaaggagcgg gcgctagggc gctggcaagt   2580
gtagcggtca cgctgcgcgt aaccaccaca cccgccgcgc ttaatgcgcc gctacagggc   2640
gcgtactatg gttgctttga cgtatgcggt gtgaaatacc gcacagatgc gtaaggagaa   2700
aataccgcat caggcgccat tcgccattca ggctgcgcaa ctgttgggaa gggcgatcgg   2760
tgcgggcctc ttcgctatta cgccagctgg cgaaagggg atgtgctgca aggcgattaa   2820
gttgggtaac gccagggttt tcccagtcac gacgttgtaa aacgacggcc agtgccaagc   2880
ttaaggtgca cggcccacgt ggccactagt acttctcgag ctctgtacat gtccgcggtc   2940
gcgacgtacg cgtatcgatg gcgccagctg cagagcgttc cagtggatat ttgctggggg   3000
ttaatgaaac attgtggcgg aacccaggga caatgtgacc aaaaaattca gggatatcaa   3060
taagtattag gtatatggat cataattgta tgcccgacta ttgcttaaac tgactgacca   3120
ctgaccttaa gagtaatggc gtgcaaggcc cagtgatcaa tttcattatt tttcattatt   3180
tcatctccat tgtccctgaa aatcagttgt gtcgccctc tacacagccc agaactatgg   3240
taaaggcgca cgaaaaaccg ccaggtaaac tcttctcaac ccccaaaacg ccctctgttt   3300
acccatggaa aaaacgacaa ttacaagaaa gtaaaactta tgtcatctat aagcttcgtg   3360
tatattaact tcctgttaca aagctttaca aaactctcat taatcctttta gactaagttt   3420 agtcagttcc aatctgaaca tcgacaaata cataaggaat tataaccata tgagttatac   3480
tgtcggtacc tatttagcgg agcggcttgt ccagattggt ctcaagcatc acttcgcagt   3540
cgcgggcgac tacaacctcg tccttcttga caacctgctt ttgaacaaaa acatggagca   3600
ggtttattgc tgtaacgaac tgaactgcgg tttcagtgca gaaggttatg ctcgtgccaa   3660
aggcgcagca gcagccgtcg ttacctacag cgtcggtgcg cttccgcat ttgatgctat   3720 cggtggcgcc tatgcagaaa accttccggt tatcctgatc tccggtgctc cgaacaacaa   3780
tgatcacgct gctggtcacg tgttgcatca cgctcttggc aaaaccgact atcactatca   3840
gttggaaatg gccaagaaca tcacggccgc agctgaagcg atttacaccc cagaagaagc   3900
tccggctaaa atcgatcacg tgattaaaac tgctcttcgt gagaagaagc cggtttatct   3960
cgaaatcgct tgcaacattg cttccatgcc ctgcgccgct cctggaccgg caagcgcatt   4020
gttcaatgac gaagccagcg acgaagcttc tttgaatgca gcggttgaag aaaccctgaa   4080
attcatcgcc aaccgcgaca agttgccgt cctcgtcggc agcaagctgc gcgcagctgg   4140
tgctgaagaa gctgctgtca aatttgctga tgctctcggt ggcgcagttg ctaccatggc   4200
tgctgcaaaa agcttcttcc cagaagaaaa cccgcattac atcggtacct catggggtga   4260
agtcagctat ccgggcgttg aaaagacgat gaaagaagcc gatgcggtta tcgctctggc   4320
tcctgtcttc aacgactact ccaccactgg ttggacggat attcctgatc ctaagaaact   4380
ggttctcgct gaaccgcgtt ctgtcgtcgt taacggcgtt cgcttcccca gcgttcatct   4440
gaaagactat ctgaccgtt tggctcagaa agttttccaag aaaaacggtg ctttggactt   4500
cttcaaatcc ctcaatgcag gtgaactgaa gaaagccgct ccggctgatc cgagtgctcc   4560
gttggtcaac gcagaaatcg cccgtcaggt cgaagctctt ctgaccccga acacgacggt   4620
tattgctgaa accggtgact cttggttcaa tgctcagcgc atgaagctcc cgaacggtgc   4680
```

-continued

```
tcgcgttgaa tatgaaatgc agtggggtca catcggttgg tccgttcctg ccgccttcgg    4740
ttatgccgtc ggtgctccgg aacgtcgcaa catcctcatg gttggtgatg gttccttcca    4800
gctgacggct caggaagtcg ctcagatggt tcgcctgaaa ctgccggtta tcatcttctt    4860
gatcaataac tatggttaca ccatcgaagt tatgatccat gatggtccgt acaacaacat    4920
caagaactgg gattatgccg gtctgatgga agtgttcaac ggtaacggtg gttatgacag    4980
cggtgctggt aaaggcctga aggctaaaac cggtggcgaa ctggcagaag ctatcaaggt    5040
tgctctggca acaccgacgg cccaacccct gatcgaatgc ttcatcggtc gtgaagactg    5100
cactgaagaa ttggtcaaat ggggtaagcg cgttgctgcc gccaacagcc gtaagcctgt    5160
taacaagctc ctctagtttt tggggatcaa ttcgagctcg gtacccaaac tagtatgtag    5220
ggtgaggtta tagctatggc ttcttcaact ttttatattc ctttcgtcaa cgaaatgggc    5280
gaaggttcgc ttgaaaaagc aatcaaggat cttaacggca gcggctttaa aaatgcgctg    5340
atcgtttctg atgctttcat gaacaaatcc ggtgttgtga agcaggttgc tgacctgttg    5400
aaagcacagg gtattaattc tgctgtttat gatggcgtta tgccgaaccc gactgttacc    5460
gcagttctgg aaggccttaa gatcctgaag gataacaatt cagacttcgt catctccctc    5520
ggtggtggtt ctccccatga ctgcgccaaa gccatcgctc tggtcgcaac caatggtggt    5580
gaagtcaaag actacgaagg tatcgacaaa tctaagaaac tgccctgcc tttgatgtca    5640 atcaacacga cggctggtac ggcttctgaa atgacgcgtt tctgcatcat cactgatgaa    5700
gtccgtcacg ttaagatggc cattgttgac cgtcacgtta ccccgatggt ttccgtcaac    5760
gatcctctgt tgatggttgg tatgccaaaa ggcctgaccg ccgccaccgg tatggatgct    5820
ctgacccacg catttgaagc ttattcttca acggcagcta ctccgatcac cgatgcttgc    5880
gccttgaagg ctgcgtccat gatcgctaag aatctgaaga ccgcttgcga caacggtaag    5940
gatatgccag ctcgtgaagc tatggcttat gcccaattcc tcgctggtat ggccttcaac    6000
aacgcttcgc ttggttatgt ccatgctatg gctcaccagt gggcggcta ctacaacctg    6060 ccgcatggtg tctgcaacgc tgttctgctt ccgcatgttc tggcttataa cgcctctgtc    6120
gttgctggtc gtctgaaaga cgttggtgtt gctatgggtc tcgatatcgc caatctcggt    6180
gataaagaag cgcagaaagc caccattcag gctgttcgcg atctggctgc ttccattggt    6240
attccagcaa atctgaccga gctgggtgct aagaaagaag atgtgccgct tcttgctgac    6300
cacgctctga agatgcttg tgctctgacc aacccgcgtc agggtgatca gaaagaagtt    6360
gaagaactct tcctgagcgc tttctaattt caaaacagga aaacggtttt ccgtcctgtc    6420
ttgattttca agcaaacaat gcctccgatt tctaatcgga ggcatttgtt tttgtttatt    6480
gcaaaaacaa aaatattgt tacaaatttt tacaggctat taagcctacc gtcataaata    6540
atttgccatt tgggatcct aattccttgg tgtaatgcca actgaataat ctgcaaattg    6600
cactctcctt caatgggggg tgcttttttgc ttgactgagt aatcttctga ttgctgatct    6660
tgattgccat cgatcgccgg ggagtccggg gcagttacca ttagagagtc tagagaatta    6720
atccatcttc gatagaggaa ttatgggga agaacctgtg ccggcggata aagcattagg    6780
caagaaattc aagaaaaaa atgcctcctg gagcattgaa gaaagcgaag ctctgtaccg    6840
ggttgaggcc tgggggcac cttattttgc cattaatgcc gctggtaaca taaccgtctc    6900
tcccaacggc gatcggggcg gttcgttaga tttgttggaa ctggtggaag ccctgcggca    6960
aagaaagctc ggcttacccc tattaattcg ttttttccgat attttggccg atcgcctaga    7020
gcgattgaat agttgttttg ccaaggcgat cgaattcgta atcatggtca tagctgtttc    7080
```

```
ctgtgtgaaa ttgttatccg ctcacaattc cacacaacat acgagccgga agcataaagt    7140
gtaaagcctg gggtgcctaa tgagtgagct aactcacatt aattgcgttg cgctcactgc    7200
ccgctttcca gtcgggaaac ctgtcgtgcc agctgcatta atgaatcggc caacgcgcgg    7260
ggagaggcgg tttgcgtatt gggcgc                                         7286

<210> SEQ ID NO 2
<211> LENGTH: 502
<212> TYPE: DNA
<213> ORGANISM: Synechocystis

<400> SEQUENCE: 2
ctgcagagcg ttccagtgga tatttgctgg gggttaatga acattgtggc cggaacccag      60
ggacaatgtg accaaaaaat tcagggatat caataagtat taggtatatg gatcataatt     120
gtatgcccga ctattgctta aactgactga ccactgacct taagagtaat ggcgtgcaag     180
gcccagtgat caatttcatt attttcatt atttcatctc cattgtccct gaaaatcagt      240
tgtgtcgccc ctctacacag cccagaacta tggtaaaggc gcacgaaaaa ccgccaggta     300
aactcttctc aaccccaaa acgccctctg tttacccatg gaaaaacga caattacaag       360 aaagtaaaac ttatgtcatc tataagcttc gtgtatatta acttcctgtt acaaagcttt     420
acaaaactct cattaatcct ttagactaag tttagtcagt tccaatctga acatcgacaa     480
atacataagg aattataacc at                                             502

<210> SEQ ID NO 3
<211> LENGTH: 1707
<212> TYPE: DNA
<213> ORGANISM: Zymomonas mobilis

<400> SEQUENCE: 3
atgagttata ctgtcggtac ctatttagcg gagcggcttg tccagattgg tctcaagcat      60
cacttcgcag tcgcgggcga ctacaacctc gtccttcttg acaacctgct tttgaacaaa     120
aacatggagc aggtttattg ctgtaacgaa ctgaactgcg gtttcagtgc agaaggttat     180
gctcgtgcca aggcgcagc agcagccgtc gttacctaca gcgtcggtgc gctttccgca     240
tttgatgcta tcggtggcgc ctatgcagaa aaccttccgg ttatcctgat ctccggtgct     300
ccgaacaaca tgatcacgc tgctggtcac gtgttgcatc acgctcttgg caaaaccgac     360
tatcactatc agttggaaat ggccaagaac atcacggccg cagctgaagc gatttacacc     420
ccagaagaag ctccggctaa aatcgatcac gtgattaaaa ctgctcttcg tgagaagaag     480
ccggtttatc tcgaaatcgc ttgcaacatt gcttccatgc cctgcgccgc tcctggaccg     540
gcaagcgcat tgttcaatga cgaagccagc gacgaagctt ctttgaatgc agcggttgaa     600
gaaaccctga aattcatcgc caaccgcgac aaagttgccg tcctcgtcgg cagcaagctg     660
cgcgcagctg gtgctgaaga agctgctgtc aaatttgctg atgctctcgg tggcgcagtt     720
gctaccatgg ctgctgcaaa aagcttcttc ccagaagaaa accgcattac catcggtacc     780
tcatggggtg aagtcagcta tccgggcgtt gaaaaagacg tgaaagaagc cgatgcggtt     840
atcgctctgg ctcctgtctt caacgactac tccaccactg gttggacgga tattcctgat     900
cctaagaaac tggttctcgc tgaaccgcgt tctgtcgtcg ttaacggcgt tcgcttcccc     960
agcgttcatc tgaaagacta tctgacccgt ttggctcaga agttccaa gaaaaccggt    1020 gctttggact cttcaaaatc cctcaatgca ggtgaactga gaaagccgc tccggctgat    1080 ccgagtgctc cgttggtcaa cgcagaaatc gcccgtcagg tcgaagctct tctgaccccg    1140
```

```
aacacgacgg ttattgctga aaccggtgac tcttggttca atgctcagcg catgaagctc    1200
ccgaacggtg ctcgcgttga atatgaaatg cagtggggtc acatcggttg gtccgttcct    1260
gccgccttcg gttatgccgt cggtgctccg aacgtcgca acatcctcat ggttggtgat     1320
ggttccttcc agctgacggc tcaggaagtc gctcagatgg ttcgcctgaa actgccggtt    1380
atcatcttct tgatcaataa ctatggttac accatcgaag ttatgatcca tgatggtccg    1440
tacaacaaca tcaagaactg ggattatgcc ggtctgatgg aagtgttcaa cggtaacggt    1500
ggttatgaca gcggtgctgg taaaggcctg aaggctaaaa ccggtggcga actggcagaa    1560
gctatcaagg ttgctctggc aaacaccgac ggcccaaccc tgatcgaatg cttcatcggt    1620
cgtgaagact gcactgaaga attggtcaaa tggggtaagc gcgttgctgc cgccaacagc    1680
cgtaagcctg ttaacaagct cctctag                                        1707

<210> SEQ ID NO 4
<211> LENGTH: 1152
<212> TYPE: DNA
<213> ORGANISM: Zymomonas mobilis

<400> SEQUENCE: 4
atggcttctt caacttttta tattcctttc gtcaacgaaa tgggcgaagg ttcgcttgaa     60
aaagcaatca aggatcttaa cggcagcggc tttaaaaatg cgctgatcgt ttctgatgct    120
ttcatgaaca atccggtgt tgtgaagcag gttgctgacc tgttgaaagc acagggtatt     180
aattctgctg tttatgatgg cgttatgccg aacccgactg ttaccgcagt tctggaaggc    240
cttaagatcc tgaaggataa caattcagac ttcgtcatct ccctcggtgg tggttctccc    300
catgactgcg ccaaagccat cgctctggtc gcaaccaatg gtggtgaagt caaagactac    360
gaaggtatcg acaaatctaa gaaacctgcc ctgcctttga tgtcaatcaa cacgacggct    420
ggtacggctt ctgaaatgac gcgtttctgc atcatcactg atgaagtccg tcacgttaag    480
atggccattg ttgaccgtca cgttaccccg atggtttccg tcaacgatcc tctgttgatg    540
gttggtatgc caaaaggcct gaccgccgcc accggtatgg atgctctgac ccacgcattt    600
gaagcttatt cttcaacggc agctactccg atcaccgatg cttgcgcctt gaaggctgcg    660
tccatgatcg ctaagaatct gaagaccgct tgcgacaacg gtaaggatat gccagctcgt    720
gaagctatgg cttatgccca attcctcgct ggtatggcct tcaacaacgc ttcgcttggt    780
tatgtccatg ctatggctca ccagttgggc ggctactaca acctgccgca tggtgtctgc    840
aacgctgttc tgcttccgca tgttctggct ataacgcct ctgtcgttgc tggtcgtctg    900
aaagacgttg gtgttgctat gggtctcgat atcgccaatc tcggtgataa agaaggcgca    960
gaagccacca ttcaggctgt tcgcgatctg gctgcttcca ttggtattcc agcaaatctg   1020
accgagctgg gtgctaagaa agaagatgtg ccgcttcttg ctgaccacgc tctgaaagat   1080
gcttgtgctc tgaccaaccc gcgtcagggt gatcagaaag aagttgaaga actcttcctg   1140
agcgctttct aa                                                       1152

<210> SEQ ID NO 5
<211> LENGTH: 606
<212> TYPE: DNA
<213> ORGANISM: Synechococcus

<400> SEQUENCE: 5
tagttaattt ttccccattg ccccaaaata catccccta aaaatatcag aatccttgcc      60
cagatgcagg ccttctggcg atcgccatgg tgagcaacga ttgcggcttt agcgttccag    120
```

```
tggatatttg ctgggggtta atgaaacatt gtggcggaac ccagggacaa tgtgaccaaa    180
aaattcaggg atatcaataa gtattaggta tatggatcat aattgtatgc ccgactattg    240
cttaaactga ctgaccactg accttaagag taatggcgtg caaggcccag tgatcaattt    300
cattattttt cattatttca tctccattgt ccctgaaaat cagttgtgtc gccctctac    360 acagcccaga actatggtaa aggcgcacga aaaccgcca ggtaaactct tctcaacccc    420
caaaacgccc tctgtttacc catggaaaaa acgacaatta caagaaagta aaacttatgt    480
catctataag cttcgtgtat attaacttcc tgttacaaag ctttacaaaa ctctcattaa    540
tcctttagac taagtttagt cagttccaat ctgaacatcg acaaatacat aaggaattat    600
aaccaa                                                               606
```

<210> SEQ ID NO 6
<211> LENGTH: 166
<212> TYPE: DNA
<213> ORGANISM: Synechococcus

<400> SEQUENCE: 6

```
tccctctcag ctcaaaaagt atcaatgatt acttaatgtt tgttctgcgc aaacttcttg     60
cagaacatgc atgatttaca aaagttgta gtttctgtta ccaattgcga atcgagaact    120
gcctaatctg ccgagtatgc aagctgcttt gtaggcagat gaacat                  166
```

<210> SEQ ID NO 7
<211> LENGTH: 568
<212> TYPE: PRT
<213> ORGANISM: Zymomonas mobilis

<400> SEQUENCE: 7

```
Met Ser Tyr Thr Val Gly Thr Tyr Leu Ala Glu Arg Leu Val Gln Ile
  1               5                  10                  15

Gly Leu Lys His His Phe Ala Val Ala Gly Asp Tyr Asn Leu Val Leu
             20                  25                  30

Leu Asp Asn Leu Leu Leu Asn Lys Asn Met Glu Gln Val Tyr Cys Cys
         35                  40                  45

Asn Glu Leu Asn Cys Gly Phe Ser Ala Glu Gly Tyr Ala Arg Ala Lys
     50                  55                  60

Gly Ala Ala Ala Ala Val Val Thr Tyr Ser Val Gly Ala Leu Ser Ala
 65                  70                  75                  80

Phe Asp Ala Ile Gly Gly Ala Tyr Ala Glu Asn Leu Pro Val Ile Leu
                 85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205
```

Arg Asp Lys Val Ala Val Leu Val Gly Ser Lys Leu Arg Ala Ala Gly
            210                 215                 220

Ala Glu Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His
            245                 250                 255

Tyr Ile Gly Thr Ser Trp Gly Val Ser Tyr Pro Gly Val Glu Lys
            260                 265                 270

Thr Met Lys Glu Ala Asp Ala Val Ile Ala Leu Ala Pro Val Phe Asn
            275                 280                 285

Asp Tyr Ser Thr Thr Gly Trp Thr Asp Ile Pro Asp Pro Lys Lys Leu
            290                 295                 300

Val Leu Ala Glu Pro Arg Ser Val Val Asn Gly Val Arg Phe Pro
305                 310                 315                 320

Ser Val His Leu Lys Asp Tyr Leu Thr Arg Leu Ala Gln Lys Val Ser
            325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
            355                 360                 365

Glu Ile Ala Arg Gln Val Glu Ala Leu Leu Thr Pro Asn Thr Thr Val
            370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
            405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
            435                 440                 445

Glu Val Ala Gln Met Val Arg Leu Lys Leu Pro Val Ile Ile Phe Leu
            450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
            485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
            515                 520                 525

Thr Asp Gly Pro Thr Leu Ile Glu Cys Phe Ile Gly Arg Glu Asp Cys
530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
            565

<210> SEQ ID NO 8
<211> LENGTH: 556
<212> TYPE: PRT
<213> ORGANISM: Zymobacter palmae

<400> SEQUENCE: 8

Met Tyr Thr Val Gly Met Tyr Leu Ala Glu Arg Leu Ala Gln Ile Gly
1               5                   10                  15

```
Leu Lys His His Phe Ala Val Ala Gly Asp Tyr Asn Leu Val Leu Leu
         20                  25                  30

Asp Gln Leu Leu Asn Lys Asp Met Glu Gln Val Tyr Cys Cys Asn
         35                  40                  45

Glu Leu Asn Cys Gly Phe Ser Ala Glu Gly Tyr Ala Arg Ala Arg Gly
     50                  55                  60

Ala Ala Ala Ala Ile Val Thr Phe Ser Val Gly Ala Ile Ser Ala Met
65                  70                  75                  80

Asn Ala Ile Gly Gly Ala Tyr Ala Glu Asn Leu Pro Val Ile Leu Ile
                 85                  90                  95

Ser Gly Ser Pro Asn Thr Asn Asp Tyr Gly Thr Gly His Ile Leu His
             100                 105                 110

His Thr Ile Gly Thr Thr Asp Tyr Asn Tyr Gln Leu Glu Met Val Lys
         115                 120                 125

His Val Thr Cys Ala Arg Glu Ser Ile Val Ser Ala Glu Glu Ala Pro
         130                 135                 140

Ala Lys Ile Asp His Val Ile Arg Thr Ala Leu Arg Glu Arg Lys Pro
145                 150                 155                 160

Ala Tyr Leu Glu Ile Ala Cys Asn Val Ala Gly Ala Glu Cys Val Arg
                165                 170                 175

Pro Gly Pro Ile Asn Ser Leu Leu Arg Glu Leu Glu Val Asp Gln Thr
             180                 185                 190

Ser Val Thr Ala Ala Val Asp Ala Ala Val Glu Trp Leu Gln Asp Arg
         195                 200                 205

Gln Asn Val Val Met Leu Val Gly Ser Lys Leu Arg Ala Ala Ala Ala
         210                 215                 220

Glu Lys Gln Ala Val Ala Leu Ala Asp Arg Leu Gly Cys Ala Val Thr
225                 230                 235                 240

Ile Met Ala Ala Glu Lys Gly Phe Phe Pro Glu Asp His Pro Asn Phe
                245                 250                 255

Arg Gly Leu Tyr Trp Gly Glu Val Ser Ser Glu Gly Ala Gln Glu Leu
             260                 265                 270

Val Glu Asn Ala Asp Ala Ile Leu Cys Leu Ala Pro Val Phe Asn Asp
         275                 280                 285

Tyr Ala Thr Val Gly Trp Asn Ser Trp Pro Lys Gly Asp Asn Val Met
         290                 295                 300

Val Met Asp Thr Asp Arg Val Thr Phe Ala Gly Gln Ser Phe Glu Gly
305                 310                 315                 320

Leu Ser Leu Ser Thr Phe Ala Ala Leu Ala Glu Lys Ala Pro Ser
                325                 330                 335

Arg Pro Ala Thr Thr Gln Gly Thr Gln Ala Pro Val Leu Gly Ile Glu
             340                 345                 350

Ala Ala Glu Pro Asn Ala Pro Leu Thr Asn Asp Glu Met Thr Arg Gln
         355                 360                 365

Ile Gln Ser Leu Ile Thr Ser Asp Thr Thr Leu Thr Ala Glu Thr Gly
         370                 375                 380

Asp Ser Trp Phe Asn Ala Ser Arg Met Pro Ile Pro Gly Gly Ala Arg
385                 390                 395                 400

Val Glu Leu Glu Met Gln Trp Gly His Ile Gly Trp Ser Val Pro Ser
                405                 410                 415

Ala Phe Gly Asn Ala Val Gly Ser Pro Glu Arg Arg His Ile Met Met
             420                 425                 430

Val Gly Asp Gly Ser Phe Gln Leu Thr Ala Gln Glu Val Ala Gln Met
         435                 440                 445
```

```
Ile Arg Tyr Glu Ile Pro Val Ile Phe Leu Ile Asn Asn Arg Gly
    450                 455                 460

Tyr Val Ile Glu Ile Ala Ile His Asp Gly Pro Tyr Asn Tyr Ile Lys
465                 470                 475                 480

Asn Trp Asn Tyr Ala Gly Leu Ile Asp Val Phe Asn Asp Glu Asp Gly
                    485                 490                 495

His Gly Leu Gly Leu Lys Ala Ser Thr Gly Ala Glu Leu Glu Gly Ala
                500                 505                 510

Ile Lys Lys Ala Leu Asp Asn Arg Arg Gly Pro Thr Leu Ile Glu Cys
                515                 520                 525

Asn Ile Ala Gln Asp Asp Cys Thr Glu Thr Leu Ile Ala Trp Gly Lys
530                 535                 540

Arg Val Ala Ala Thr Asn Ser Arg Lys Pro Gln Ala
545                 550                 555

<210> SEQ ID NO 9
<211> LENGTH: 383
<212> TYPE: PRT
<213> ORGANISM: Zymomonas mobilis

<400> SEQUENCE: 9

Met Ala Ser Ser Thr Phe Tyr Ile Pro Phe Val Asn Glu Met Gly Glu
1               5                   10                  15

Gly Ser Leu Glu Lys Ala Ile Lys Asp Leu Asn Gly Ser Gly Phe Lys
            20                  25                  30

Asn Ala Leu Ile Val Ser Asp Ala Phe Met Asn Lys Ser Gly Val Val
        35                  40                  45

Lys Gln Val Ala Asp Leu Leu Lys Ala Gln Gly Ile Asn Ser Ala Val
50                  55                  60

Tyr Asp Gly Val Met Pro Asn Pro Thr Val Thr Ala Val Leu Glu Gly
65                  70                  75                  80

Leu Lys Ile Leu Lys Asp Asn Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
        115                 120                 125

Pro Ala Leu Pro Leu Met Ser Ile Asn Thr Thr Ala Gly Thr Ala Ser
130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
            180                 185                 190

Met Asp Ala Leu Thr His Ala Phe Glu Ala Tyr Ser Ser Thr Ala Ala
        195                 200                 205

Thr Pro Ile Thr Asp Ala Cys Ala Leu Lys Ala Ala Ser Met Ile Ala
210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Tyr
            260                 265                 270
```

-continued

Tyr Asn Leu Pro His Gly Val Cys Asn Ala Val Leu Leu Pro His Val
                275                 280                 285

Leu Ala Tyr Asn Ala Ser Val Val Ala Gly Arg Leu Lys Asp Val Gly
        290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ser Ile Gly Ile
                325                 330                 335

Pro Ala Asn Leu Thr Glu Leu Gly Ala Lys Lys Glu Asp Val Pro Leu
                340                 345                 350

Leu Ala Asp His Ala Leu Lys Asp Ala Cys Ala Leu Thr Asn Pro Arg
                355                 360                 365

Gln Gly Asp Gln Lys Glu Val Glu Glu Leu Phe Leu Ser Ala Phe
                370                 375                 380

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 10
ggagtaagca tatgagttat actg                                          24

<210> SEQ ID NO 11
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 11
ggatctcgac tctagaggat cc                                            22

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide primer

<400> SEQUENCE: 12
gtcagttcca atctgaacat cga                                           23

<210> SEQ ID NO 13
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 13
aatttgtaac cgtagttctg ggat                                          24

<210> SEQ ID NO 14
<211> LENGTH: 25
<212> TYPE: DNA
<213> ORGANISM: Artificial Sequence
<220> FEATURE:
<223> OTHER INFORMATION: synthetic oligonucleotide primer

<400> SEQUENCE: 14

```
ttggtgattt tgaactttg cttgc                                          25
```

<210> SEQ ID NO 15
<211> LENGTH: 22
<212> TYPE: DNA
<213> ORGANISM: Artificial Sequence
<220> FEATURE:
<223> OTHER INFORMATION: synthetic oligonucleotide primer

<400> SEQUENCE: 15

```
ttgcaagcga tttcgagata aa                                            22
```